United States Patent
Modi et al.

(10) Patent No.: US 6,306,391 B1
(45) Date of Patent: Oct. 23, 2001

(54) PREPARATION OF AN ORAL PHARMACEUTICAL FORMULATION CONTAINING AN ANTI-INFECTIVE AGENT AND A MICROORGANISM

(75) Inventors: Rajiv Indravadan Modi; Yatish Kumar Bansal; Bakulesh Mafatlal Khamar, all of Ahmedabad (IN)

(73) Assignee: Cadila Pharmaceuticals, Ltd., Ahmedabad (IN)

( * ) Notice: Subject to any disclaimer, the term of this patent is extended or adjusted under 35 U.S.C. 154(b) by 0 days.

(21) Appl. No.: 09/045,890

(22) Filed: Mar. 23, 1998

(30) Foreign Application Priority Data

Mar. 27, 1997 (IN) .............................. 174/BOM/97

(51) Int. Cl.$^7$ .............................. A01N 63/00; C12N 1/20
(52) U.S. Cl. .................................... 424/93.44; 424/93.46; 435/252.9; 435/253.4
(58) Field of Search .............................. 424/93.44, 93.45; 435/253.4, 252.9

(56) References Cited

FOREIGN PATENT DOCUMENTS

| | | |
|---|---|---|
| 0306465 | 3/1989 | (EP) . |
| 4430M | 9/1966 | (FR) . |
| 5247M | 7/1967 | (FR) . |
| 6855M | 5/1969 | (FR) . |
| 53-052612 | 5/1978 | (JP) . |
| 1083025 | 3/1989 | (JP) . |
| 9640179 | 12/1961 | (WO) . |

OTHER PUBLICATIONS

Black et al., Scand. J. of Infec. Dis./23(2), 247–254, 1991.*

* cited by examiner

*Primary Examiner*—David M. Naff
*Assistant Examiner*—Mike Meller

(57) ABSTRACT

A process of making a stable fixed dose oral pharmaceutical formulation is provided. The formulation contains at least one anti-infective agent and at least one microorganism. The process involves a step of first coating the agent and/or the microorganism to provide a protective barrier around it. Next, the process involves a step of combining the agent and the microorganism into a single pharmaceutical formulation in the form of a capsule or a tablet. The barrier protects the microorganism from the effect of the anti-infective agent to maintain the microorganism in a viable form for a period of at least three months. The agent can be an antibiotic such as amoxycillin and the microorganism can be *Lactobacillus acidophilus*.

16 Claims, No Drawings

PREPARATION OF AN ORAL PHARMACEUTICAL FORMULATION CONTAINING AN ANTI-INFECTIVE AGENT AND A MICROORGANISM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a process of manufacturing a formulation containing anti-infective agent(s) with viable organisms which are susceptible to anti-infective agents. Micro organisms are used to prevent adverse effects like diarrhoea caused by anti-infective agents.

The present invention is directed to manufacturing of a formulation wherein anti-infective agents and susceptible viable organisms are combined in that micro organisms, though susceptible to anti-infective agent, remain viable for the shelf life of a formulation or until they are consumed. Susceptible organisms are usually combined with anti-infective agents to prevent or minimise adverse effects of anti-infective agents like diarrhoea, pseudomembranous colitis, mega colon, etc.

Organisms are classified as pathogens and commonsals. Pathogens are responsible for various infectious diseases and are not normally present in that part of the body. They are also known as infectious agents. Commonsals are normally present in various parts of the body and perform useful functions. They provide vitamin K, B-12, Thiamine, Riboflavin etc. to the body.[1] They inhibit the growth of pathogens by variety of mechanisms.[2] Anti-infective agents are used to treat/prevent infectious diseases. They kill organisms by various ways. However they are not always specific for pathogens and also kill commonsals.[2] Destruction or reduction in the number of commonsals results in loss of function of commonsals and various effects of these are seen.[2,5] These effects are known as adverse effects or side effects of anti-infective therapy. Diarrhoea with or without super-infection is one of such effects seen with anti-infective therapy.[3,4,6] Diarrhoea is seen as an adverse reaction to many antibiotics, but it is most commonly seen with broad spectrum antibiotics. The incidence of diarrhoea also depends on level of absorption from G.I. It is less frequent with those getting completely absorbed compared to incompletely absorbed. It also depend on the amount of drug used. The antibiotics causing diarrhoea include clindamycin, ampicillin, amoxycillin, cephalosporins (e.g. cefuroxime axetil, cefixime. cepahlexin ceftriaxone), amoxycillin+ clauvanic acid, ampicillin+salbcutam, fluoroquinolens and other combinations of broad spectrum antibiotics, e.g. amoxycillin+cloxacillin.[3,5,6,7,8,9,10,11,12,13,14,15,16,18] Diarrhoea can be benign and secondary to transient dysfunction of normal colonic flora due to anti-infective agents[6] or super-infection by pathogens like clostridium difficile following alteration of normal flora by anti-ineffective agents.[7,4,19,20] Management in such an event requires cessation of anti-infective therapy[3,7,4] and use of other therapies. Other therapies which can be used include different kind of anti-infective agents e.g. metronidazole, vancomycin,[3,13,8] teicoplanin and/or use of organisms like lactobacilli, biofidobacterium, saccharomyies boulardili, streptococcus thermophilus, enterococcus facecium SF 68, L Casei GG etc.[14,15,16] These can be combined with whole bowel irrigation with good results.[17] The organisms used[9] eradicate or help in eradicating pathogens by a variety of mechanisms, which include production of hydrogen peroxide or inhibition or adherence of pathogens to intestinal cells. Anti-infective agents induced diarrhoea prolongs-treatment and increases the cost of therapy by increased number of[1] drugs to be used,[2] days of hospitalisation and [3]consultations. Sometimes it creates a life threatening situation e.g. pseudememberous colitis,[4,13,20] toxic megacolon.

The organisms named above can be used to treat diarrhoea when it occurs. They can also be used to prevent diarrhoea.[14,16,18] Commercially available preparations include lactobacillus alone (Lactiflora, Lactobacil, Lactocap, Lactovit, Sporlac) or in combination with streptococcus (Lacticyn) or Sacchromyces (Laviest). To prevent diarrhoea organisms are given along with the anti-infective agents. This requires consumption of minimum two different drugs i.e. an anti-infective agent and an organism. This decreases compliance of a patient.

Attempts have been made to put organisms and anti-infective agents into one formulation. Some of these are commercially available. Lactobacillus is commonly used organism. Anti-infective agents used in the formulation include ampicillin, (e.g. Alcillin plus from Alpine), amoxicycillin (e.g. Alox plus from Alpine), ampicillin+cloxacillin (e.g. Amplus from Jagsonpal, Elclox plus from Elder, Penmix plus from Dee Pharma, Pen plus from Systopic, Poxin Plus from Alpine), amoxicycillin+cloxacillin (e.g. Bicidal plus from Kee Pharma, Diclox from Croford Pharma, Twinclox plus trom Alpine). They all are simple admixture of anti-infective agents and susceptible organisms. However, analysis of commercially available, as well as prepared by us revealed that organisms incorporated into formulation does not remain viable and did not perform any useful function for which they were to be used. Neither organisms nor their activity could be detected as early as 7 days after putting lactobacilli with various antibiotics like ampicillin, amoxycillin, amoxycillin+cloxacillin etc. or in commercially available preparation. Though 60 million spores are put into formulation, none of them could be grown or demonstrated viable on glucose yeast extract agar plate. It also failed to produce lactic acid as evaluated by consumption of NaOH.

REFERENCES

1. Gastrointestinal tracts chapter 65 in Text Book of Medical Physiology ed. Arther C Guyton & John E. Hall Publishers Prism Books (Pvt.) Ltd., 9th edition 1996
2. pp. 1042 antimicrobial agents chapter 44 in the Pharmacological Basis of Therapeutics in Goodman & Gillman
3. PP-586 antibiotic associated colitis Chapter 14 in Current Medical Diagnosis & Treatment 36th edition.
4. A. P. Ball, Chapter 7, Toxicity in antibiotic and chemotherapy seventh edition. edit. Francis O'Gerard
5. Betalactam therapy and intestinal flora Journal of Chemother. May 1995; 7 suppl 1: 25–31
6. Diarrhoea caused by antibiotic therapy. Rev-Prat. Jan. 15, 1996; 46(2): 171–6
7. Antibiotic associated diarrhoea in light of personal observations. Pol-Tyg-Lek. September 1995; 50(36): 45–9
8. Antibiotic-induced colitis. Semin-Pediatr-Surg. November 1995; (4(4): 215–20
9. Clostridium difficile acquisition rate and its role in nosocomial diarrhoea at a university hospital in Turkey. Eur-J-Epidemiol. August 1996; 12(4): 391–4

10. Risk factors associated with Clostridium difficile diarrhoea in hospitalized adult patients: a case-control study—sucralfate ingestion is not a negative risk factor. Infect-Control-Hosp-Epidemiol. April 1996; 17(4): 232–5
11. Clinical comparison of cefuroxime axetil and amoxycillin/clavulanate in the treatment of patients with secondary bacterial infections of acute bronchitis. Clinical Ther. September–October 1995; 17 (5): 861–74
12. Clinical comparison of cefuroxime axetil suspension and amoxycillin/lavulanate suspension in the treatment of paediatric patients with acute otitis media with effusion. Clinical Ther. September–October 1995; 17(5): 838–51
13. Antibiotic-associated pseudomembranous colitis: retrospective study of 48 cases diagnosed by colonoscopy. Therapie. January–February 1996; 51(1): 81–6
14. Biotherapeutic agents. A neglected modality for the treatment and prevention of selected intestinal and vaginal infections. JAMA Mar. 20, 1996; 275(11): 870–6
15. The pharmacologic principles of medical practice, Krantz & Carr
16. Prevention of beta-lactam-associated diarrhoea by saccharomyces boulardii compared with placibo. Am.J.Gastroenterol. March 1995; 90(3): 439–48
17. Whole-bowel irrigation as an adjunct to the treatment of chronic, relapsing Clostridium difficile colitis. J-Clin-Gastroenterol. April 1996; 22(3): 186–9
18. Prophylaxis against ampicillin-associated diarrhoea with a lactobacillus preparation. Am.J.Hosp.Pharm. June 1979; 36: 754–757
19. Clostridium difficile in antibiotic associated pediatric diarrhoea. Indian Pediatr. February 1994; 31(2): 121–6
20. Side effects and consequences of frequently used antibiotics in clinical practice. Schweiz-Med-Wochenschr. Mar. 30, 1996; 126(13): 528–34.

BRIEF SUMMARY OF THE INVENTION

The objective of present invention is to combine susceptible organisms into a pharmaceutical composition containing anti-infective agents and keep them viable for the shelf life of the formulation until it is consumed.

The further objective of present invention is to minimise side effects of anti-infective agents resulting from destruction/alteration of normal flora by providing viable organisms along with anti-infective agent(s).

The further objective of present invention is to provide a pharmaceutical composition which is effective after longer period of storage.

The further objective of this present invention is to increase compliance by reduction/elimination in side effects of anti-infective agents.

The further objective of the present invention is to improve compliance by providing two drugs in one pharmaceutical composition.

The further objective of present invention is to provide organism at a desired site.

The following specification particularly describes and ascertain the nature of this invention and manner in which it is to be performed.

The anti-infective agent and organisms are to be identified. Their dosage route of administration and dosage form is finalised.

The susceptible organisms are combined into the formulation in such a way that organisms remain viable for the shelf life of a formulation in spite of being in contact with anti-infective agent. To protect susceptible organisms from effect of anti-infective agent a protective barrier is created around organisms or anti-infective agent, in such a way that anti-infective agent cannot have effect on organisms. This results in viable organisms in presence of anti-infective agent. The organism remains viable as long as the barrier is maintained. This is like applying paint or a film on a substance to prevent corrosion by isolating it from surroundings.

The protective barrier is selected depending on route of administration and dosage form of the pharmaceutical composition (anti-infective agent+organism).

The pharmaceutical composition so manufactured is evaluated for stability and efficacy.

The pharmaceutical composition so manufactured is evaluated at different test conditions of temperature and humidity (45° C., 37° C. at 80% relative humidity and ambient temperature) for time interval extending up to 12 months.

The samples of formulation were taken for study at 3 weeks intervals. Samples were analysed for presence of organisms by quantitative and qualitative microbiological techniques. These values were found to be comparable with amount of organisms introduced into formulation.

The samples of formulation were also analysed for presence of anti-infective agent by quantitative estimation. The values of anti-infective agents forms were found to be comparable to those introduced into the formulation.

Thus findings indicate presence of organism and anti-infective agent in same amount when formulation was evaluated at different time interval after it was exposed to different environment.

The formulations so created were found to have improved therapeutic efficacy in term of reduction/elimination of antibiotic induced diarrhoea.

DETAILED DESCRIPTION OF THE INVENTION

Usually ampicillin causes maximum diarrhoea amongst penicillin. The reported incidence is as high as 20% with ampicillins. In 40 patients when ampicillin+lactobacilli were given in a pharmaceutical composition prepared as described in this application, none of them developed diarrhoea and everybody could complete the full course of antibiotic therapy. The non development of diarrhoea suggests efficacy of new pharmaceutical composition prepared according to present invention.

1. Following are examples of formulations containing various anti-infective agents and susceptible organisms. However, it is not intended that the scope of this invention be limited by these examples.

| Example I | | Example II | |
|---|---|---|---|
| Ampicillin | 250 mgm | Ampicillin | 500 mgm |
| Lactobacillus | 60 million | Lactobacillus | 60 million |
| Example III | | Example IV | |
| Amoxycillin | 250 mgm | Amoxycillin | 500 mgm |
| Lactobacillus | 60 million | Lactobacillus | 60 million |
| Example V | | Example VI | |
| Cloxacillin | 250 mgm | Cloxacillin | 500 mgm |
| Lactobacillus | 60 million | Lactobacillus | 60 million |

-continued

| Example VII | | | Example VIII | | |
|---|---|---|---|---|---|
| Ampicillin | 250 | mgm | Ampicillin | 125 | mgm |
| Cloxacillin | 250 | mgm | Cloxacillin | 125 | mgm |
| Lactobacillus | 60 | million | Lactobacillus | 30 | million |
| Example IX | | | Example X | | |
| Amoxycillin | 250 | mgm | Amoxycillin | 125 | mgm |
| Cloxacillin | 250 | mgm | Cloxacillin | 125 | mgm |
| Lactobacillus | 60 | million | Lactobacillus | 30 | million |
| Example XI | | | Example XII | | |
| Ampicillin | 1000 | mgm | Ampicillin | 250 | mgm |
| Sultamicin | 500 | mgm | Probenecid | 250 | mgm |
| Lactobacillus | 60 | million | Lactobacillus | 60 | million |
| Example XIII | | | Example XIV | | |
| Amoxycillin | 250 | mgm | Amoxycillin | 500 | mgm |
| Clavulanic acid | 125 | mgm | Probenecid | 500 | mgm |
| Lactobacillus | 60 | million | Lactobacillus | 60 | million |
| Example XV | | | Example XVI | | |
| Amoxycillin | 250 | mgm | Amoxycillin | 250 | mgm |
| Bromhexine | 8 | mgm | Carbocisteine | 150 | mgm |
| Lactobacillus | 60 | million | Lactobacillus | 60 | million |
| Example XVII | | | Example XVIII | | |
| Amoxycillin | 500 | mgm | Amoxycillin | 500 | mgm |
| Bromhexine | 8 | mgm | Carbocisteine | 150 | mgm |
| Lactobacillus | 60 | million | Lactobacillus | 60 | million |
| Example XIX | | | Example XX | | |
| Cephalexin | 250 | mgm | Cephalexin | 500 | mgm |
| Lactobacillus | 60 | million | Lactobacillus | 60 | million |
| Example XXI | | | Example XXII | | |
| Cephalexin | 250 | mgm | Cephalexin | 250 | mgm |
| Bromhexine | 4 | mgm | Probenecid | 250 | mgm |
| Lactobacillus | 60 | million | Lactobacillus | 60 | million |
| Example XXIII | | | Example XXIV | | |
| Cephalexin | 500 | mgm | Cefuroxime Axetil | 125 | mgm |
| Probenecid | 500 | mgm | Lactobacillus | 60 | million |
| Lactobacillus | 60 | million | | | |
| Example XXV | | | Example XXVI | | |
| Cefuroxime Axetil | 250 | mgm | Cefuroxime Axetil | 500 | mgm |
| Lactobacillus | 60 | million | Lactobacillus | 60 | million |
| Example XXVII | | | Example XXVIII | | |
| Cefixime | 200 | mgm | Cefixime | 400 | mgm |
| Lactobacillus | 60 | million | Lactobacillus | 60 | million |

In above examples anti-infective agents can be used for any therapeutic purpose which in a therapeutic dosage causes significant adverse effects which can be prevented by using an organism. The organism can be any which prevents or minimises adverse reactions of anti-infective agents when taken at same time. For prevention of diarrhoea, pseudomembranous colitis it can be biofidobacterium, sacchormyces streptococcus thermophilus, enterococcus etc. instead of lactobacillus in above examples in their appropriate dosages.

2. Following are examples of providing barrier to organisms for different dosage forms. However, it is not intended that the scope of this invention be limited by these examples.

Example I

Capsules:
  i) Organisms can be lumped together and formulated into a tablet. The tablet is coated with a barrier film. The film protected organisms are introduced into the capsule independently. Anti-infective agent is put in the capsule containing organisms protected by a barrier film. It can be vice versa.
  ii) Organisms can be granulated. Granules containing organisms are coated whit a barrier film. Barrier film coated granules are mixed with anti-infective agent before filling them into capsules.

Example II

Tablets
  i) Layered tablets: Organisms are coated and compressed into a layer of tablet. The other layer(s) of tablet contains anti-infective agent.
  ii) Tablet containing mixture: Granules of organisms are coated with barrier film and mixed with granulated material of anti-infective agents and compressed into a tablet.
  iii) Coated Tablets: Anti-infective agents are formulated into compressed tablet. They are coated. During coating stage organisms are introduced in the coating. The coating should be capable of protecting organisms from anti-infective agents. It can be vice versa i.e. anti-infective agent is included in coating.
  iv) Tablet with a hole is produced containing anti-infective agent. The hole of the tablet is filled with organisms. The tablet so obtained may be coated for final finishing.

Coating/barrier protection is not so much necessary as it is in a capsule form as long as moisture content is controlled and physical separation is maintained in a same tablet. Formulated tablet can be dispersible tablet or simple tablet.

Example III

Liquid Formulations:
  i) The organisms are coated with barrier film mixed with other ingredients (dry form) of formulation including anti-infective agent. The product is reconstituted before use by addition of adequate amount of liquid.
  ii) The organisms are coated with barrier film and suspended in a liquid containing anti-infective agents or vice versa. The barrier film is stable in liquid formulation but disintegrates in body due to alteration in surrounding, e.g. pH 3. Following are examples of coating agents which can be used in making stable fixed dose pharmaceutical composition containing anti-infective agent(s) and micro organism. However, it is not intended that the scope of this invention be limited by these examples.

| Chemical Name | Trade Name |
|---|---|
| 1. Cellulose acetate phthalate | Aquateric CAP Cellacefate |
| 2. Poly(butyl methacrylate, (2-dimethyl aminoethyl) methacrylate, methyl methacrylate) 1:2:1 | Eudragit E 100 Eudragit E 12.5 |
| 3. Poly(ethyl acrylate, methyl methacrylate) 2:1 | Eudragit NE 30D (formerly Eudragit 30D) |
| 4. Poly(methacrylic acid, methyl methacrylate) 1:1 | Eudragit L 100 Eudragit L 12.5 |
| 5. Poly(methacrylic acid, ethyl acrylate) 1:1 | Eudragit L 12.5 P Eudragit L 30 D-55 Eudragit L 100-55 |

-continued

| Chemical Name | Trade Name |
|---|---|
| 6. Poly(methacrylic acid, methyl methacrylate) 1;2 | Eudragit S 100 |
| | Eudragit S 12.5 |
| | Eudragit S 12.5 P |
| 7. Poly(ethyl acrylate, methyl methacrylate, trimethylaminonioethyl methacrylate chloride) 1:2:0.2 | Eudragit RL 100 |
| | Eudragit RL PO |
| | Eudragit RL 30 D |
| | Eudragit RL 12.5 |
| 8. Poly(ethyl acrylate, methyl methacrylate, trimethylammonioethyl methacrylate chloride) 1:2:0.1 | Eudragit RS 100 |
| | Eudragit RS PO |
| | Eudragit RS 30 D |
| | Eudragit RS 12.5 |
| 9. Hydrogenated Castor Oil | Castrowax |
| | Castrowax MP 70 |
| | Castrowax MP 80 |
| | Opalwax |
| | Simulsol |
| 10. Cetyl Alcohol | Crodacol C70 |
| | Crodacol C9O |
| | Crodacol C95 |
| 11. Diethyl Phthalate | Kodaflex DEP |
| | Palatinol A |
| 12. Ethyl cellulose | Aquacoat |
| | Ethocel |
| | Surelease |
| 13. Hydroxypropyl Cellulose | Klucel |
| | Methocel |
| | Nisso HPC |
| 14. Hydroxypropyl Methylcellulose Phthalate | — |
| 15. Zein | — |

4. Following are examples of methods of preparing fixed dose stable pharmaceutical composition. However, it is not intended that the scope of this invention be limited by these examples.

EXAMPLE I

Double Layered Tablet

A stable fixed dose combination layered tablet is prepared using the following components of which the active ingredients are anti-infective agent(s) and micro organisms. The remaining components are physiologically acceptable excipients. One of the active ingredients is coated in a coating pan by the coating process known to those skilled in the art. Excipients are also used along with one of the active ingredients (granules) during tablet making for lubrication as required for the purpose. Granules of separate active ingredients are first prepared by process known to those skilled in the art. The separate sets of granules are then compressed on double rotary tablet compression machine having a laying facility at a temperature below 25° C. and relative humidity not more than 50% by processes known to those skilled in the art and the tablets are transferred to a coating pan for film coating to be given by using film coating process known to those skilled in the art.

i) The relative proportion of anti infective agents and excipients to prepare coating suspension and coating anti-infective agents before granulation:

| Ingredients | Parts by weight |
|---|---|
| Anti infective agent | 77.54% |
| Ethyl cellulose | 2.70% |
| Isopropyl alcohol | 7.42% |
| Dichloromethane | 12.34% | ii) The relative proportion of anti-infective agents and excipients to prepare granules:

| Ingredients | Parts by weight |
|---|---|
| Anti-infective agent | 64.08% |
| Microcrystalline cellulose | 26.45% |
| Starch | 9.00% |
| Colour Sunset Yellow Lake | 0.45% |
| Purified water | 0.02% | iii) The relative proportion of excipients to be added to granules containing anti-infective agents as lubricants:

| Ingredients | Parts by weight |
|---|---|
| Sodium chloride | 31.91% |
| Polyplasdone XL | 14.89% |
| Microcrystalline cellulose | 21.28% |
| Saccharine sodium | 10.64% |
| Flavour orange | 10.64% |
| Magnesium stearate | 5.32% |
| Purified Talc | 5.32% | iv) The relative proportion of micro organisms and excipients to prepare granules:

| Ingredients | Parts by weight |
|---|---|
| Micro organisms | 18.18% |
| Starch | 18.18% |
| Microcrystalline cellulose | 56.67% |
| Magnesium stearate | 0.91% |
| Polyplasdone XL | 3.03% |
| Sodium chloride | 3.03% |

The fixed dose layered tablet compositions which are prepared through making use of above described process contain the above active ingredients anti-infective agents and viable organisms in their respective therapeutic concentration. The compositions provide pharmacological effects which are complementary to the effects produced by (Prior art) each individual ingredient and are stable for a period of atleast 3–36 months at ambient room temperature.

EXAMPLE II

Capsules

Stable fixed dose combination capsules are prepared using following components of which the active ingredients are anti-infective agents and micro organisms. The remaining components are physiologically acceptable excipients. Granules of one of the active ingredients (e.g. micro organisms) are first prepared by process known to those skilled in the art. The granules so formed are compressed into a tablet by tablet compression machine heaving a laying facility at a temperature below 25° C. and relative humidity not more than 50% by process known to those skilled in the art. Tablets are transferred to a coating pan for coating to be given by coating process known to those skilled in the art.

The remaining active ingredient is mixed with excipients and filled into gelatin capsules by process known to those skilled into the art. Before sealing of capsules the coated tablet containing active ingredients are introduced into capsule by processes known to those skilled in the art.

i) The relative proportion of anti-infective agent and excipients for filling in capsule:

| Ingredients | Parts by weight |
| --- | --- |
| Anti-infective agent | 91.94% |
| Pregelatinised starch | 6.24% |
| Magnesium stearate | 1.44% |
| Sodium lauryl sulfate | 0.38% | ii) The relative proportion of micro organism and excipients to prepare granules as follows:

| Ingredients | Parts by weight |
| --- | --- |
| Micro organism | 42.86% |
| Micro crystalline cellulose | 53.93% |
| Magnesium stearate | 1.07% |
| Colloidal silicone dioxide | 0.71% |
| Cross carmellose sodium | 1.43% | iii) The relative proportion of excipients to prepare coating suspension for coating of a tablet containing micro organisms to be kept into a capsule:

| Ingredients | Parts by weight |
| --- | --- |
| Hydroxy propyl methyl cellulose Phthalate | 4.37% |
| Titanium dioxide | 0.96% |
| Purified Talc | 0.19% |
| Polyethylene glycol | 0.99% |
| Isopropyl alcohol | 34.95% |
| Dichloromethane | 58.54% |

The fixed dose capsule compositions which are prepared through making use of above described process contain the above active ingredients, anti infective agents and viable organisms in their respective therapeutic concentrations. The compositions provide pharmacological effect which are complementary to the effects produced by (prior art) each individual ingredient and are stable for at least 3–36 months at ambient room temperature.

EXAMPLE III

Liquid Suspension

A stable fixed dose combination liquid tablet is prepared using the following components of which the active ingredients are anti-infective agent(s) and micro organisms. One of the active ingredients is granulated after suspending it in a coating suspension to provide granules of 100 micron or less in size by processes known to those skilled in art. Granules so prepared are suspended into a liquid formulation by processes known to those skilled in the art. The other active ingredient is introduced into the suspension by the process known to those skilled in the art in such a way that final concentration of micro organisms is 20% of anti infective agent(s).

The relative proportion of anti-infective agent and excipients to prepare coated granules:

| Ingredients | Parts by weight |
| --- | --- |
| Anti infective agent | 56.82% |
| Cellulose acetate pthalate | 22.73% |
| Isopropyl alcohol | 6.82% |
| Dichloromethane | 13.63% |

The fixed dose liquid suspension composition which is prepared through making use of above described process contains the above active ingredients, anti infective agents and viable organisms in their respective therapeutic concentrations. The composition provides pharmacological effects which are complementary to the effects produced by (prior art) each individual ingredient and are stable for at least 3–36 months at ambient room temperature.

EXAMPLE IV

Dry Powder Composition to Make Liquid Composition After Reconstitution.

A stable fixed dose combination dry powder for reconstituting liquid formulation before use is prepared using the following components of which the active ingredients are anti-infective agent(s) and micro organisms. The remaining components are physiologically acceptable excipients.

One of the active ingredients is granulated after suspending it in a coating suspension by process known to those skilled in the art. The granules so prepared are dried and mixed with dry powder containing another active ingredient by processes known to those skilled in the art in such a way that micro organisms are 20% of anti infective agent(s) by weight.

The relative proportion of anti infective agents and the excipients to prepare coated granules is as follows:

| Ingredients | Parts by weight |
| --- | --- |
| Anti infective agent(s) | 50% |
| Hydroxy propyl methyl cellulose K-15 M (1,00,000 cps) | 45% |
| Purified water | 5% |

The fixed dose dry powder compositions which are prepared through making use of above described process contain the above active ingredients, anti infective agents and viable organisms in their respective therapeutic concentrations. The composition provide pharmacological effects which are complementary to the effects produced by (prior art) each individual ingredient and are stable for at least 3–36 months at ambient room temperature.

Above composition when reconstituted by adding liquid prior to use remains stable at ambient room temperature for 3 to 7 days.

5. Following are examples of therapeutic dosage of various anti-infective agents and micro organisms. However, it is not intended that the scope of this invention be limited by these examples.

A. Anti-infective Agents

Anti infective agents can be penicillins e.g. ampicillin, amoxycillin, cloxacillin, cephalosporins e.g. cephalexin, cefadroxyl, cefuroxime axetil, cefixime, beta lactamase inhibition like clauvanic acid—macrolide like erythromycin as single ingredient or combination thereof.

i. Solid dosage forms like capsules or tablet contains anti infective agents equivalent to 125, 250 or 500 mgm of active component ii. Liquid dosage forms usually contains anti infective agents equivalent to 125 mgm of active component in 5 ml.

B. Micro Organism Which Can Be Used for Therapeutic Purposes and the Dosage are as Under:

| | | |
|---|---|---|
| 1. | Lactobacillus Aciophillus | 10 to 100 million |
| 2. | Lactobacillus Spores | 30–60 × 10$^6$ |
| 3. | Lactobacillus Lactis | 10–500 million |
| 4. | Streptococcus thermophilus | 10 million |
| 5. | Streptococcus lactis | 10 million |
| 6. | Saccromyces cerevisea | 10 million |
| 7. | Lactobacilli GG | 10$^{10}$ units |

We claim:

1. A process to provide a stable fixed dose oral pharmaceutical formulation comprising at least one anti-infective agent as a first active ingredient and at least one micro organism susceptible to said anti-infective agent as a second active ingredient, the process consisting essentially of a step of coating at least one of the first and second active ingredients to provide a protective barrier around the active ingredient, and thereafter a step of combining the active ingredients into a single pharmaceutical formulation selected from the group consisting of a tablet and a capsule wherein said tablet or capsule contains both said anti-infective agent and said micro organism, the protective barrier protects the susceptible micro-organism from the effect of the anti-infective agent to maintain the susceptible micro-organism in a viable form for a period of at least three months, said anti-infective agent is selected from the group consisting of Ampicillin, Amoxycillin, Cloxacillin, Clavulanic acid, Sultamicin, Cefuroxime axetil, Cefadroxyl, Cephalexin, Cefixime, Erythromycin, Ciprofloxacin, and combinations thereof, and said micro organism is selected from the group consisting of *Lactobacillus acidophilus, Lactobacillus spores, Lactobacillus lactis, Streptococcus thermophilus, Streptococcus lactis, Saccromyces cerevisea, Lactobacilli GG*, and combinations thereof.

2. A process as claimed in claim 1 wherein the anti-infective agent and the micro organisms are separately admixed with physiologically acceptable excipients.

3. A process as claimed in claim 1 which process comprises admixing separately the anti-infective agent and the micro organism with a physiologically acceptable excipient to provide granules of the anti-infective agent and the micro organism, and coating at least one of the anti-infective agent granules and the micro organism granules, and subsequently compressing said anti-infective agent granules and said micro organisim granules into a layered tablet such that one layer contains the anti-infective agent and the other layer contains the micro organism.

4. A process as claimed in claim 3 wherein the excipient is ethyl cellulose and said coating is performed by suspending the granules to be coated in a suspension containing ethyl cellulose dissolved in isopropyl alcohol and dichloromethane.

5. A process as claimed in claim 4 wherein the excipient is a mixture of microcrystalline cellulose, and starch.

6. A process as claimed in claim 3 wherein the excipient is a mixture of magnesium stearate, polyplasdone XL and sodium chloride.

7. A process as claimed in claim 1 wherein one of the active ingredients is compressed into a tablet and coated, and said coated tablet is put into a capsule containing the other active ingredient.

8. A process as claimed in claim 7 wherein said tablet contains said micro organism admixed with physiologically acceptable excipients.

9. A process as claimed in claim 7 wherein coating to produce the coated tablet is carried out by using a coating suspension comprising hydroxy propyl methyl cellulose phthalate, titanium dioxide, talc, polyethelene glycol, isopropyl alcohol, and dichloro methane.

10. A process as claimed in claim 1 wherein a mixture is formed containing the anti-infective agent and a mixture of physiologically acceptable excipients containing pregelatinised starch, magnesium stearate, and sodium lauryl sulfate, and the mixture containing the anti-infective agent and the excipients is subsequently filled into capsules.

11. A process as claimed in claim 1 wherein coating of the anti-infective agent is carried out by using a coating suspension comprising cellulose acetate phthalate, isopropyl alcohol, and dichloromethane.

12. A process as claimed in claim 1 wherein the anti-infective agent is coated in a coating suspension comprising hydroxy propyl methyl cellulose and purified water.

13. A stable fixed-dose oral pharmaceutical composition prepared by the process of claim 1.

14. The stable pharmaceutical composition of claim 13 wherein the ratio of anti-infective agent to micro organism is in the range of 2:1 to 25:1.

15. The stable pharmaceutical composition of claim 14 wherein the ratio of anti-infective agent to micro organism is about 5:1.

16. The stable pharmaceutical composition of claim 13 wherein the coating comprises a compound selected from the group consisting of cellulose acetate phthalate; poly (butylmethacrylate, (2-dimethyl aminoethyl) methacrylate, methyl methaacrylate); poly(ethyl acrylate, methyl methacrylate); poly(methacrylic acid, methyl methacrylate); poly(methacrylic acid, ethyl acrylate); poly(ethyl acrylate, methyl methacrylate, trimethylammonioethyl methacrylate chloride), hydrogenated Castor oil; Cetyl alcohol; diethyl phthalate; ethyl cellulose; hydroxypropyl cellulose; hydroxypropyl methylcellulose phthalate; and zein.

\* \* \* \* \*